United States Patent [19]

Asano

[11] Patent Number: 4,478,212
[45] Date of Patent: Oct. 23, 1984

[54] ADAPTER FOR COUPLING A CAMERA WITH AN ENDOSCOPE

[75] Inventor: Sheiji Asano, Saitama, Japan

[73] Assignee: Fuji Photo Optical Co., Ltd., Saitama, Japan

[21] Appl. No.: 436,061

[22] Filed: Oct. 22, 1982

[30] Foreign Application Priority Data

Oct. 22, 1981 [JP] Japan .......................... 56-157482[U]

[51] Int. Cl.³ .............................................. A61B 1/06
[52] U.S. Cl. ......................................... 128/6; 354/62
[58] Field of Search ........................................ 128/4–8; 354/62; 200/51 R

[56] References Cited

U.S. PATENT DOCUMENTS 3,318,216  5/1967  Hajjar et al. .......................... 354/62
4,273,431  6/1981  Farmer et al. ......................... 354/62
4,407,272  10/1983  Yamaguchi ............................ 128/6

Primary Examiner—Edward M. Coven
Assistant Examiner—Max F. Hindenburg
Attorney, Agent, or Firm—Young & Thompson

[57] ABSTRACT

An adapter for coupling a camera adapted to receive electric power from an endoscope to which the camera is coupled, to an endoscope having no function of electric power transmission. The adapter is coupled between the ocular section of the endoscope and the mounting of the taking lens of the camera and has electric power output terminals for providing the camera with electric power. The adapter can have a built-in power source or a plug-in power source.

5 Claims, 1 Drawing Figure

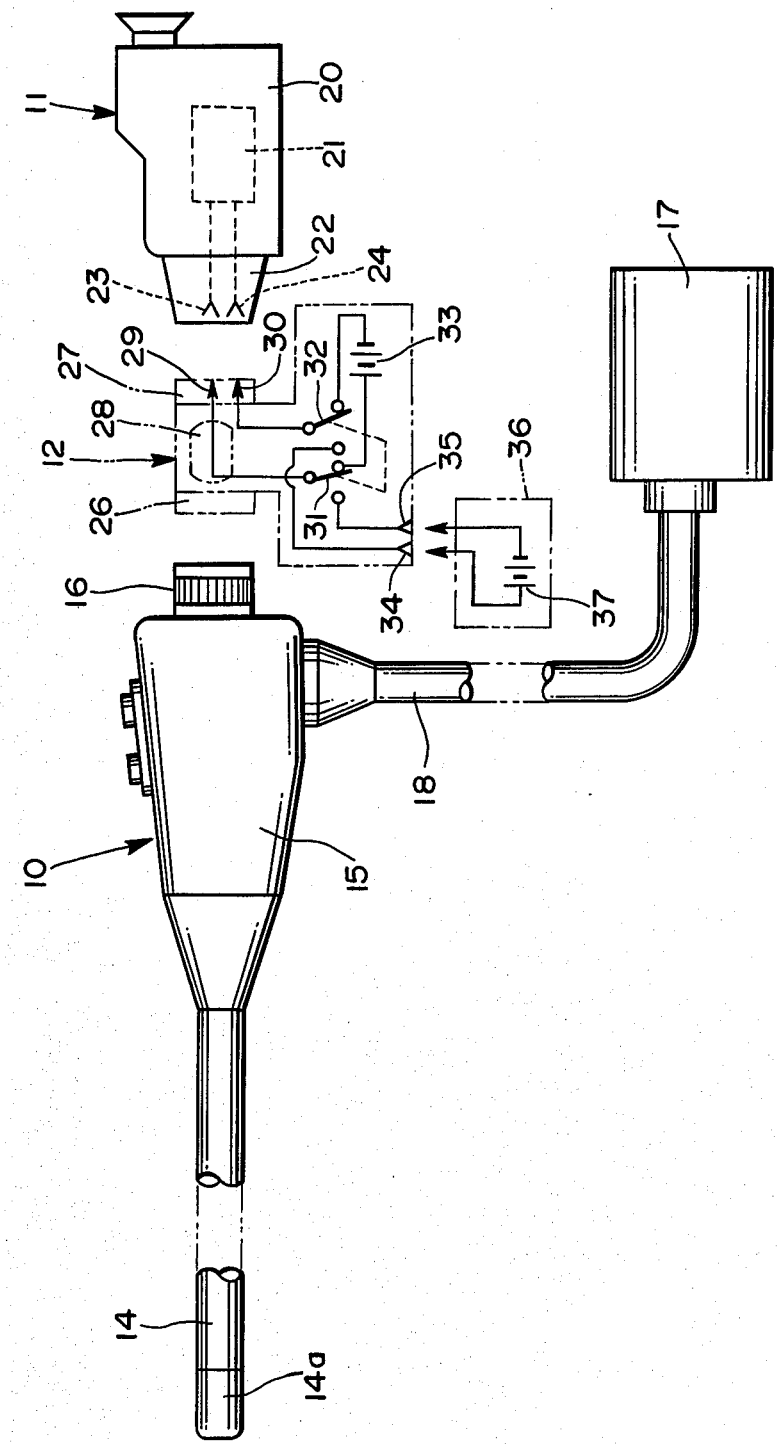

ADAPTER FOR COUPLING A CAMERA WITH AN ENDOSCOPE

BACKGROUND OF THE INVENTION

The present invention relates to an adapter for coupling a camera with an endoscope at the ocular section thereof, more particularly to an adapter by which an endoscope of the type having no function of electric power-transmission to a camera to be coupled therewith, and a camera of the type adapted to receive electric power from an endoscope to which the camera is coupled, can be coupled in successful combination.

Endoscopes are widely used for the purpose of observing or examining inaccessible cavities of a human body or industrial apparatus which are impossible to be observed or examined directly from the outside. A camera is coupled to a endoscope to photograph an image formed by the endoscope, while visually observing the image. In order to allow a camera to be coupled to an endoscope, the endoscope has a mounting means such as bayonet pawls or screw threads at the rear end of the ocular section thereof.

There are two types of endoscopes on the market, one of which has a function of electric power-transmission to a camera including electric apparatus such as an electric shutter, and the other of which has no such function. On the other hand, there are also two types of cameras for endoscopes, one of which is adapted to receive electric power from the endoscope on which the camera is mounted, and the other of which has an electric power source built therein or a special electric power source unit externally thereof. The former endoscope has electric wires for power transmission in its flexible connector section connectable to an illuminating light source including an electric power source. One end of the respective wire is connected to a power output terminal disposed on a mounting plate of the ocular section of the endoscope, and the other end is connected to a power input terminal at the rear end of the flexible connector section. Connecting the endoscope at the rear end of the flexible connector section to the illumination light source unit, the electric power source is electrically connected to the power output terminals of the ocular section through the wires in the flexible section. This type of endscope is so designed as to be used with a camera which is adapted to receive electric power from the endoscope. Thus, upon connecting the camera to the endoscope, the contact between the output terminals of the endoscope and the input terminals of the camera provides the camera with electric power supply from the electric power source of the illuminating light source of the endoscope. As a result, the camera is made operative.

The latter type of camera, which has an electric power source included therein or a special electric power source externally thereof can be offered in combination with all types of endoscopes. On the other hand, the former type of camera, which is adapted to receive electric power from endoscopes, cannot be used in successful combination with endoscopes without electric wires therein.

OBJECTS OF THE INVENTION

It is therefore a principal object of the present invention to provide an adapter by which a camera of the type having an adapter to receive electric power from an endoscope can be used in successful combination with an endoscope without electric wires therein.

It is another object of the present invention to provide such an adapter which provides an electric connection between a camera and a power source so as to supply electric power to the camera through the adapter when the camera is connected to the adapter.

SUMMARY OF THE INVENTION

According to the invention, the above and other objects are achieved by an adapter for coupling a camera to an endoscope, which is provided with power output terminals connected to a power source so that an electric connection between the camera and the power source is provided through a connection of the power output terminals with power input terminals of the camera when the camera is connected thereto.

By using the adapter according to the invention from which a camera connected thereto can receive electric power, a camera having no electric power source therein can be used in successful combination with an endoscope without electric wires therein. The adapter can expand the area of application of a camera having no electric power therein, whereby users can save a great deal of expense.

BRIEF DESCRIPTION OF THE DRAWING

The various features of novelty which characterize the invention are set forth with particularity in the following specifications. For a better understanding of the invention, its operating advantages, and the specific objects attained by its use, reference should be had to the accompanying drawing and description in which there is illustrated and described a preferred embodiment of the invention.

In the drawing, the single FIGURE is a schematic diagram of a preferred embodiment of the present invention.

DETAILED DESCRIPTION OF THE INVENTION

Referring now to the FIGURE, there is illustrated an adapter 12 according to the present invention by which an endoscope 10 having no electric wires, and a camera 11 adapted to receive electric power from an endoscope, can be coupled together. The endoscope 10 comprises a flexible elongated section 14 insertable into cavities of a human body, for instance, a remote control section 15 for moving the tip 14a of the flexible elongated section 14 in any direction desired, an ocular section 16, and an elongated connector section 18 connectable to an illuminating light source unit 17. In the flexible elongated section or insertion section 14, an image-transmitting optical fiber bundle extends from the tip to the ocular section, and a light-transmitting optical fiber bundle extends from the tip 14a to the light source unit 17 through the connector section 18. The insertion section 14 is provided at the tip thereof with an objective facing the light-incident end of the image-transmitting optical fiber bundle, and the ocular section 16 is provided with an ocular assembly behind the opposite end of the image-transmitting optical fiber bundle. Because endoscopes having a contruction as described above are well known to those skilled in the art, no more detailed description of the endoscope or its operation is needed.

The camera 11 is provided in the main body 20 thereof with conventional camera control circuits 21 such as an automatic exposure control circuit, an automatic film advancing control circuit, and the like, which are connected to electric power input terminals 23 and 24 on the mounting of the taking lens 22. The lens mounting is provided with a well-known connecting means, for instance a plurality of bayonet pawls or screw threads, detachably engageable with their counterparts on the ocular section 16 of the endoscope. A more specific description of such a camera 11 for direct connection to an endoscope is omitted in this specification because the construction and function thereof are well known to those skilled in the art.

The camera 11 for use with an endoscope is adapted to be used in combination with any endoscope of the well-known type which has electric wires extending from the end of the connector section to the ocular section through the connector section. Thus, such a camera cannot be used in successful combination with an endoscope 10 (shown in the FIGURE) without electric wires because of the absence of electric power for the camera from the endoscope 10.

However, by using the adapter according to the present invention, the camera 11 and the endoscope 10 can be coupled in successful combination. For this purpose, the adapter 12 at opposite sides has connector means 26 and 27 such as bayonet pawls, screw threads, or the like which are detachably engageable with their counterparts on the ocular section 16 and the camera 11, respectively. Upon coupling the camera 11 to the endoscope 10 by the adapter 12, the axes of the ocular assembly of the endoscope 10 and the objective assembly of the camera 11 are optically aligned. Furthermore, the adapter 12 may be provided with an optical compensation system 28 therein if necessary.

The adapter 12 described above is provided the connector means 27 to which the camera 11 is electrically connected by power output terminals 29 and 30. Connecting the camera 11 to the adapter 12 completes an electrical connection therebetween through the output and input terminals 29, 30 and 23, 24, respectively, so as to power the camera control circuits 21. The output terminals 29 and 30 can be connected either to a built-in electric power source 33 in the adapter 12 or to a special plug-in electric power source 37 in an external power unit 36 through external input terminals 34 and 35 by means of a changeover switch 31, 32 which is externally operated.

As has been described in the foegoing, electrical coupling of the camera control circuits 21 of the camera 11 and the built-in power source 33 or the special plug-in electrical power sorce 37 through the connections between terminals 23 and 29, and 24 and 30 can be achieved at the time the camera 11 is coupled to the endoscope 10 by the adapter 12, whereby the camera 11 is made operable for performing endoscopic photography, while the camera 11 is optically coupled to the endoscope 10.

What is claimed is:

1. An adapter for coupling a camera having electrical control circuits with an endoscope having an ocular section, said camera being of the type having camera control circuits adapted to receive electric power through an endoscope to which the camera is coupled, and said endoscope having no function of electric power-transmission to a camera which is coupled thereto, said adapter comprising:
   first means for detachably coupling the adapter to the endoscope at the ocular section of the endoscope;
   second means for detachably coupling the adapter to the camera; and
   electric power output terminals disposed in said second means for electrically connecting the control circuits of said comara to an electric power source separate from said endoscope, whereby said camera control circuits can receive electric power.

2. An adapter as defined in claim 1, wherein said adapter further comprises a built-in electrical power source.

3. An adapter as defined in claim 1, wherein said adapter further comprises electric power input terminals by which said electric power output terminals can be connected to a plug-in electrical power source.

4. An adapter as defined in claim 3, wherein said adapter further comprises a changeover switch by which said electrical power output terminals are selectively connected to either of said built-in or plug-in electric power sources.

5. An adapter as defined in claim 1, and an optical compensation system in the adapter between the ocular section of the endoscope and the camera.

* * * * *